United States Patent [19]
Vollrath et al.

[11] Patent Number: 5,964,695
[45] Date of Patent: Oct. 12, 1999

[54] NON-INVASIVE PENILE ERECTION DEVICE

[76] Inventors: Andrew J. Vollrath; Ji Ji Secong Vollrath, both of 3524 Superior Ave., Sheboygan, Wis. 53083

[21] Appl. No.: 08/892,719

[22] Filed: Jul. 15, 1997

Related U.S. Application Data

[63] Continuation of application No. 08/583,781, Jan. 11, 1996, abandoned.

[51] Int. Cl.⁶ ......................................................... A61F 5/41
[52] U.S. Cl. ............................................................... 600/38
[58] Field of Search .......................................... 600/38–41

[56] References Cited

U.S. PATENT DOCUMENTS

| | | |
|---|---|---|
| 4,641,638 | 2/1987 | Perry . |
| 4,723,538 | 2/1988 | Stewart et al. . |
| 4,753,227 | 6/1988 | Yanuck, Jr. . |
| 4,856,498 | 8/1989 | Osbon . |
| 5,020,522 | 6/1991 | Stewart . |
| 5,125,890 | 6/1992 | Merrill et al. ............................. 600/39 |
| 5,234,402 | 8/1993 | Obson ....................................... 600/41 |
| 5,306,227 | 4/1994 | Osbon et al. ............................. 600/41 |
| 5,344,389 | 9/1994 | Walsdorf et al. ......................... 600/41 |

FOREIGN PATENT DOCUMENTS

| | | |
|---|---|---|
| 347300 | 8/1960 | Switzerland . |
| 83211373 | 2/1996 | Taiwan . |

*Primary Examiner*—Samuel Gilbert
*Attorney, Agent, or Firm*—Jeffrey S. Sokol; Sokol Law Office

[57] ABSTRACT

The present invention relates to a non-invasive penile erection device having a constrictor ring designed to fit against the base of a male genital or penis, and a diaphragm seal that forms a substantially air tight seal against the constrictor ring. The constrictor ring is designed to comfortably and securely fit the base of the penis. The substantially air tight seal enables the pump to produce vacuum pressures of over 17 inches of mercury. The placement of the constrictor ring on the base of the penis and the greater vacuum pressure achieved by the device tend to draw the root of the penis into the constrictor ring so that a more natural erection is achieved and maintained after the vacuum tube is removed. The erection device can be easily provided as a kit containing a rigid vacuum tube, a hand or power operated pump, and several diaphragm seals and constrictor rings of various sizes to achieve a custom fit and optimum results.

14 Claims, 4 Drawing Sheets

NON-INVASIVE PENILE ERECTION DEVICE

This application is a continuation of U.S. patent application Ser. No. 08/583,781, filed Jan. 11, 1996, now abandoned.

TECHNICAL FIELD

The present invention relates to a non-invasive penile erection device having a diaphragm that seals against a constrictor ring placed at the base of the male genital to provide a comfortable customized fit at greater vacuum pressures and produces a more natural erection.

BACKGROUND PRIOR ART

A variety of non-invasive, vacuum type penile inflation devices are available. These inflation devices use external vacuum pressure to replace the body's natural ability to inflate the male genital or penis with blood. The devices typically utilize a cylindrically shaped vacuum tube for receiving the penis, a diaphragm for sealing the open end of the vacuum tube around the penis and a pump for evacuating or removing air from the vacuum tube. When air is removed from inside the tube, the decrease in pressure causes blood to enter and inflate the male genital. A constrictor ring is typically placed around the male genital after it is inflated to maintain the inflated state of the penis when the vacuum tube is removed. Examples of such devices are shown in U.S. Pat. No. 4,641,638 to Perry, U.S. Pat. No. 4,753,227 to Yanuck, Jr., U.S. Pat. No. 4,856,498 to Osbon, U.S. Pat. No. 5,125,890 to Merrill, and U.S. Pat. No. 5,344,389 to Walsdorf, the contents of which are incorporated by reference.

One shortcoming of conventional penile inflation devices is that the diaphragm does not form a sufficiently air tight seal to produce a desired amount of vacuum pressure inside the tube. Even when gel lubricants are applied to the diaphragm and male genital to improve the seal, air tends to leak between the diaphragm and the male genital. This air leakage reduces the amount of vacuum pressure attained inside the tube and the amount of inflation and stiffness of the male genital. Conventional penile inflation devices achieve about 14 to 16 inches of mercury of vacuum pressure, while a fully inflated, usable erection often requires about 17 to 22 inches of mercury of vacuum pressure.

An additional shortcoming with the prior art is that the inflation devices do not inflate and maintain the penis in an erect and usable position. Conventional constrictor rings are designed to fit on and secure to the substantially flat shaft portion of the penis. The rings are not intended to fit around the increasingly larger diametered base of the penis located adjacent the groin of the individual, especially when inflated. The increasingly wider base creates a slope that causes the constrictor ring to slide off the base and onto the shaft of the penis. Conventional constrictor rings are also not designed to allow the root of the penis, which extends inwardly of the groin of the individual, to be drawn into the constrictor ring. When the vacuum tube is removed, only that portion of the shaft of the penis downstream of the constrictor ring remains inflated. The base and root of the penis remain or return to a flaccid state and the penis does not achieve and maintain a natural erect position.

A still further problem with the prior art is that the flaccid base and root portions of the penis upstream of the constrictor ring create a "joint" about which the inflated shaft portion of the penis may bend. The inflated portion of the penis must be manipulated by hand during use, which can be especially difficult for paraplegic and quadriplegic individuals or their partner.

A further problem of the prior art is that conventional constrictor rings used in various inflation devices are painful due to their narrow width and generally "rubber band" like shape. The edges of the constrictor ring dig into the skin of the individual and cause substantial pain.

A still further problem with conventional designs is that it is difficult to position the constrictor ring on the base or root of the male genital after it is placed on the penis. The user must grip the edges of the narrow rubber band shaped constrictor ring to adjust the constrictor ring and attempt to work it onto the base after its initial placement on the shaft of the penis. This can be quite difficult when the edges of the constrictor ring are digging into the skin.

A still further problem of conventional designs is that the lubricants used to help form the seal between the diaphragm and the male genital are messy. Lubricant invariably spreads all over the inflation device, the hands and body of the individual, and the surroundings.

A still further problem of the prior art is that the diaphragm and constrictor ring do not fit all individuals with equal comfort and equal results. Different individuals require differently sized constrictor rings and diaphragms. A trial and error approach to obtaining a correctly sized constrictor ring and diaphragm can be inconvenient and embarrassing given the nature of the product involved.

A still further problem with the prior art assemblies is that the manufacturing costs can be excessive. The cost and number of components making up the penile erection device should be kept to a minimum. The erection device should also cooperate with existing vacuum tube and pump designs when possible to avoid expensive and time consuming manufacturing modifications.

The present invention is provided to solve these and other problems.

SUMMARY OF THE INVENTION

The present invention relates to a non-invasive penile erection device having a constrictor ring designed to fit against the base of a male genital or penis, and a diaphragm seal that forms a substantially air tight seal against the constrictor ring. The constrictor ring is designed to comfortably and securely fit the base of the penis. The substantially air tight seal enables the pump to produce vacuum pressures of over 17 inches of mercury. The placement of the constrictor ring on the base of the penis and the greater vacuum pressure achieved by the device tend to draw the root of the penis into the constrictor ring so that a more natural erection is achieved and maintained after the vacuum tube is removed. The erection device can be provided as a kit containing a rigid vacuum tube, a hand or power operated pump, and several diaphragm seals and constrictor rings of various sizes to achieve a custom fit and optimum results.

One advantage of the present invention is its ability to inflate the shaft, base and root portions of the male genital. The constrictor ring is designed to securely fit the base of the penis and draw a portion of the root of the penis into the constrictor ring when vacuum pressure is applied to the inside of the vacuum tube. The inflation of the base and root portions of the penis causes the penis to rise to a more natural erect position. The constrictor ring also maintains the penis in an erect position after the vacuum tube is removed.

An additional advantage of the present invention is that the hands of the individual may remain free during use because the base of the penis does not become flaccid after the vacuum tube is removed to form a "joint" about which the shaft of the penis can bend.

A further advantage of the present invention is that the constrictor ring is designed to be easily positioned onto the base of the male genital with the tabs of the ring abutting the groin of the individual. The tabs of the constrictor ring enable the individual to work the ring securely onto the increasing diameter or sloped shape of the base of the male genital. The constrictor ring is shaped to have an increasing inside diameter down the length of the ring moving from the outer edge of the tubular portion to the inner end of the conical portion. This increasing inside diameter enables the ring to stay fixed on the base of the penis both during inflation and use without sliding down the shaft of the penis.

A still further advantage of the present invention is that the inner and outer ends of the constrictor ring are rounded to provide a comfortable fit by helping to prevent the constrictor ring from digging into the skin of the individual.

A still further advantage of the present invention is that the diaphragm is designed to form a substantially air tight seal against the constrictor ring. The tubular portion of the constrictor ring has a predetermined diameter that increases slightly moving from the outer end toward the inner end of the constrictor ring. The inner end of the diaphragm has a thick, rounded shank with a predetermined diameter that is substantially equivalent to the diameter of the outer end of the tubular portion of the constrictor ring. When air is removed from the vacuum tube, the tubular portion of the constrictor ring slides into the diaphragm mouth to form a relatively air tight seal. This seal enables the vacuum pump to obtain a sufficient level of vacuum pressure to inflate the penis and draw a portion of the root of the penis into the constrictor ring. This allows the penis to achieve a more natural erection both while the vacuum tube is in use and after the vacuum tube has been removed.

A still further advantage of the present invention is that no messy lubricants are necessary to form the seal between the constrictor ring and the diaphragm.

A still further advantage of the present invention is its reliability and ease of use. A loader is provided for placing the ring on the base of the penis. The tabs enable the individual to slide the ring from the narrow receiving end, down the length of the loader to its wider open end. After the penis is inserted into the open end of the loader, the individual can grip the tabs to pull the ring off the loader and onto the base of the penis. The tabs also permit the individual to further advance the ring down the base of the penis so that a portion of the root of the penis can be inflated during use. The ease with which an individual can position the constrictor ring on the base of the penis helps ensure that a more natural erection is attained by the individual during each use.

A still further advantage of the present invention is that a plurality of differently sized diaphragm seals and constrictor rings can be provided in a kit that includes all the penile erection device components. The individual can select the diaphragm and constrictor ring that fits them best for a customized, comfortable fit that produces good results in the privacy of their own home. Inconvenient and embarrassing trips to a doctor or store are not necessary.

A still further advantage of the present invention is found in its inexpensive component costs and its relative ease of manufacture. For example, the present vacuum tube can be manufactured using relatively inexpensive conventional plastic tubes. The flexible diaphragm and constrictor ring designs can be efficiently incorporated into a conventional vacuum tube and pump designs so that expensive and time consuming manufacturing costs are avoided.

Other features and advantages of the invention will be apparent from the following specification taken in combination with the following drawings.

DETAILED DESCRIPTION

Figure 1:
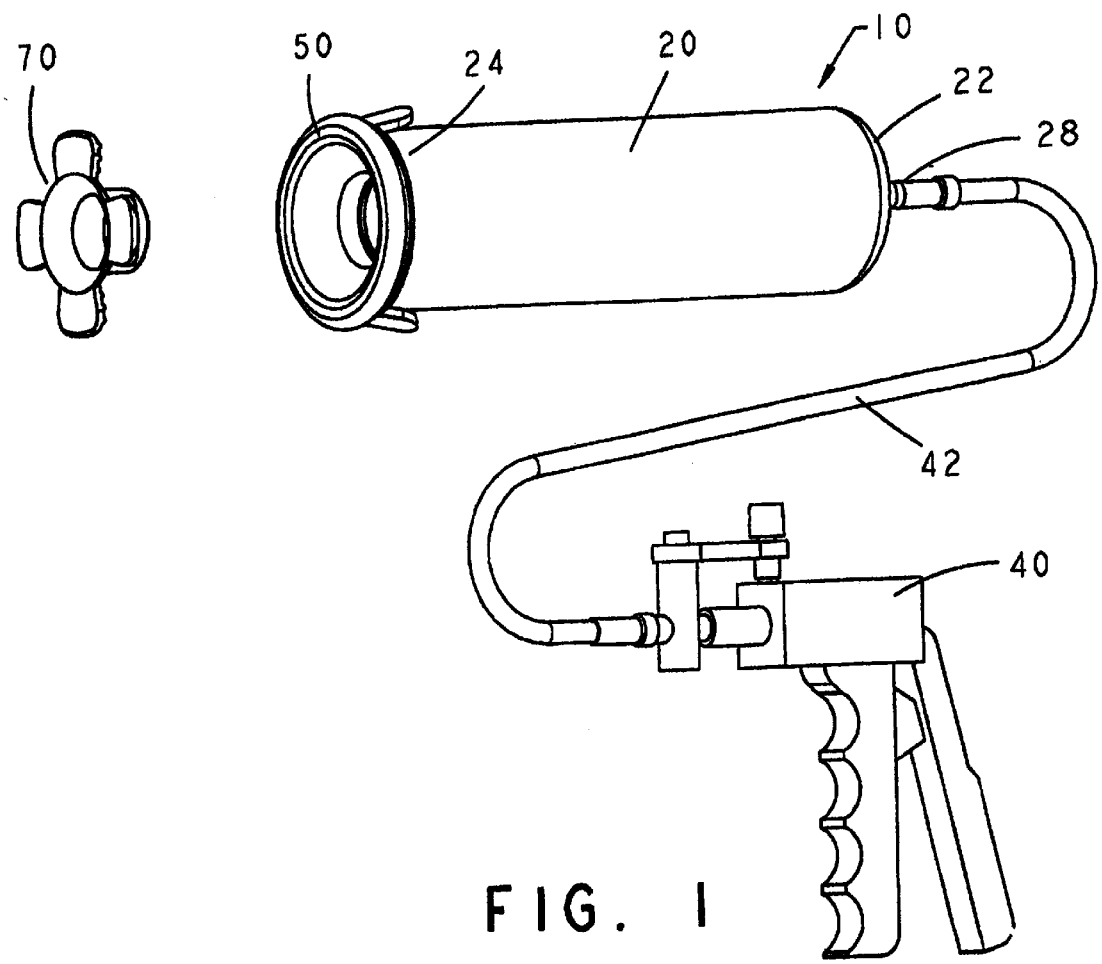
FIG. 1 is a perspective view of a penile erection device of the present invention including a constrictor ring and a vacuum tube equipped with a hand pump at one end and a diaphragm seal at the other end.

While this invention is susceptible of embodiments in many different forms, there is shown in the drawings and will herein be described in detail, a preferred embodiment of the invention with the understanding that the present disclosure is to be considered as an exemplification of the principles of the invention and is not intended to limit the broad aspects of the invention to the embodiment illustrated.

As shown in FIG. 1, the present invention relates to a vacuum type penile erection device for a male genital 5 having a shaft portion 6, a base portion 7 and a root portion 8. The erection device 10 includes a vacuum tube 20 into which the male genital 5 is inserted, a hand pump 40 for evacuating or removing air from the tube, a flexible diaphragm 50 that forms a seal around the male genital and a constrictor ring 70 for maintaining the penis in an erect position after the vacuum tube has been removed.

The vacuum tube 20 is a conventional, generally cylindrically shaped tube having a predominantly closed end 22, an open end 24 with a diameter of about two inches and an inside surface 25 for receiving the male genital. The tube 20 is preferably made of a rigid, transparent plastic having a thickness of about 0.1 of an inch. The tube 20 is designed to maintain its shape when at least about 24 inches of mercury in vacuum pressure are achieved inside the tube. An outwardly projecting lip 26 is formed around the circumference of the open end 24. The lip 26 has a height of about 0.25 of an inch and its edges are rounded for comfort. The predominantly closed end 22 of tube 20 has a nippled opening 28 through which air is removed from inside the tube 20. The tube 20 is sized and shaped to accommodate the male genital of a variety of individuals.

The pump 40 is used to evacuate or remove air from the vacuum tube 20 through the nippled opening 28. A flexible hose 42 connects the nippled opening 28 to the pump 40. The pump 40 should be capable of achieving vacuum pressures in excess of 24 inches of mercury. The pump 40 should also have a safety valve or vacuum limiter (not shown) set to open at 24 inches of mercury to prevent harmful vacuum pressures from being imparted to the individual during use. In this way, the pump 40 can experience a reduction in achievable vacuum pressure due to wear and tear over time, without affecting the performance of the device 10. While FIG. 1 shows a conventional hand operated pump 40 for removing or evacuating air from the tube 20, it should be understood that other evacuating means, such as a motorized pump, could be employed without departing from the invention.

Figure 2:
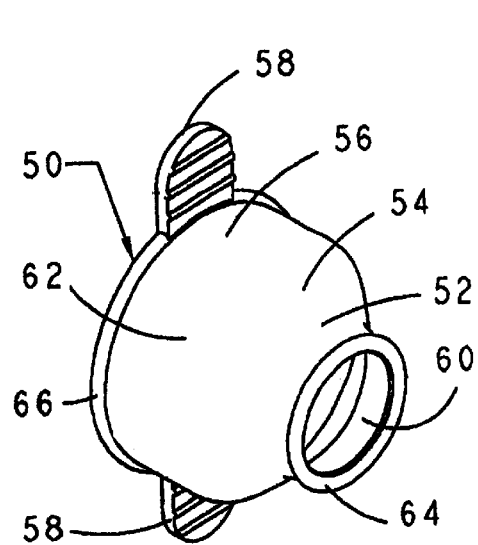
FIG. 2 is a perspective view of the diaphragm seal in its relaxed position before placement on the vacuum tube.

As shown in FIG. 2, the diaphragm seal 50 is made of an integral piece of soft, durable and flexible rubber to facilitate comfort and bending and stretching during use. Although the diaphragm seal 50 is preferably made of synthetic natural rubber, it should be understood that other materials having similar qualities may be used. A product similar to the diaphragm seal 50 used in the present invention is available through Da Goang Assorted Co., Ltd. of Taipei, Taiwan.

As shown in FIG. 2, the diaphragm seal 50 has a generally tubular shape when in its relaxed position. The diaphragm seal 50 has an inner end 52, a middle portion 54, an outer end 56. The inner end 52, middle portion 54 and outer end 56 are integrally formed and have a substantially uniform thickness when in a relaxed state. The inner and outer ends 52 and 56 of the diaphragm seal 50 form inner and outer openings, respectively, having predetermined diameters. The diameter of the inner opening of the inner end 52 seals against the constrictor ring 70 as discussed below. The diameter of the outer opening is sized so that the outer end 56 can be stretched to fit over and seal against the lip 26 of vacuum tube 20. The inner and outer ends 52 and 56 each have an integral shank 64 and 66, respectively, with a substantially circular cross-sectional area. The shanks 64 and 66 are thicker and more stretch resistant than the walls of the inner and outer ends 52 and 56.

As shown in FIGS. 4–7, the outer end 56 of the diaphragm seal 50 is folded over the lip 26 of the open end 24 of the vacuum tube 20. Two handles 58 are formed integrally with and extend outwardly from opposite sides of the outer end 56 of the diaphragm seal 50. The thicker and more stretch resistant outer shank 66 helps maintain the air tight seal between the outer end 56 of the diaphragm seal 50 and the lip 26 of the vacuum tube 20. The handles 58 enable the individual using the device to easily release the diaphragm seal 50 from the vacuum tube 20 after the male genital has been inflated to an erect position, as will be discussed later.

The constrictor ring 70 is an integral piece of soft, durable and flexible rubber to facilitate comfort and bending and stretching during use. Although the constrictor ring is preferably made of synthetic natural rubber, it should be understood that other materials having similar characteristics may be used.

As best shown in FIGS. 3 and 10–12, the constrictor ring 70 has a tubular portion 72 located proximal its outer end 73, a conical portion 74 located proximal its inner end 75, and several tabs 76 projecting outwardly from the inner end of the conical portion. The tubular portion 72 has a length of about 0.50 of an inch and thicknesses of about 0.045 of an inch. The conical portion 74 has a length of about 0.25 of an inch and a varying thickness due to its rounded inside surface 80. The conical portion 74 is generally larger than that of the tubular portion 72. The tubular portion 72 forms an opening having a predetermined diameter of about one inch at the outer end 73 for receiving the male genital 5.

The inner and outer ends 75 and 73 of the constrictor ring 70 are rounded for comfort and ease of use. The inside surface 80 of the inner end 75 is rounded to a radius of about 0.25 of an inch to provide a comfortable fit and accommodate the typically thicker diameter of the base 7 of the male genital 5. Although the inside surface 80 of the inner end 75 is stated to be rounded, it should be understood that the inside surface may have a different arcuate shape. The outside surface 82 of the conical portion 74 is chamfered at about a 45 degree angle. The outer end 73 of the constrictor ring 70 is rounded on both its inside and outside surfaces 80 and 82 to a radius of about 0.01 of an inch. The inside surface 80 of the outer end 73 is rounded to provide a comfortable fit. The outside surface 82 of the outer end 73 is rounded to facilitate sliding engagement of the inner shank 64 of the diaphragm seal 50 during use, as will be discussed later. The inside diameter of the inside surface 80 of the tubular portion 72 increases slightly and continuously heading away from outer end 73 and toward inner end 75. The increase in inside diameter is more pronounced in the conical portion 74 due to the rounding of the inside surface 80 of the inner end 75 as discussed above. The continuously increasing diameter of the inside surface 80 enables the individual to fit the constrictor ring onto the base 7 of the penis 5 and helps maintain the ring at this location during use. The continuously increasing diameter of the inside surface 80 also helps form the substantially air tight seal between the diaphragm 50 and the constrictor ring 70. Although the constrictor ring 70 is shown as having a conical portion 74 with a chamfered outside surface 82 that meets the tubular portion 72 at about a 45 degree angle, it should be understood that the outside surface 82 of the conical and tubular portions could form a continuous arcuate or rounded shape.

Figure 10:
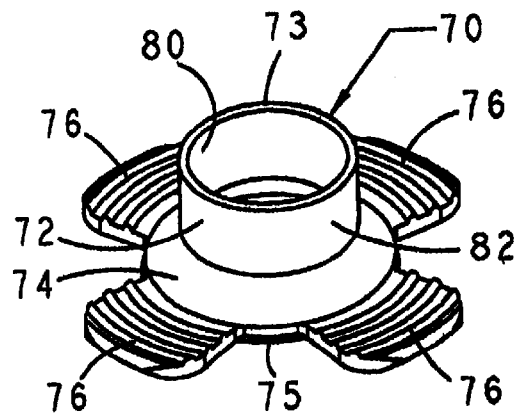
FIG. 10 is a perspective view of the constrictor ring with a four tab design.
Figure 11:
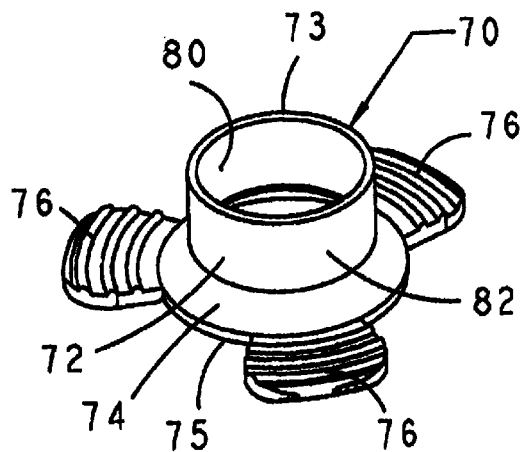
FIG. 11 is a perspective view of the constrictor ring with a three tab design.
Figure 12:
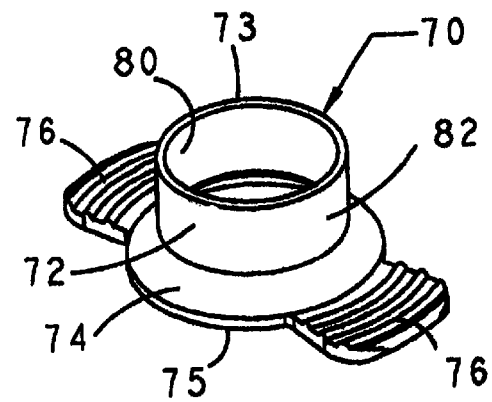
FIG. 12 is a perspective view of the constrictor ring with a two tab design.

As best shown in FIGS. 10–12, the tabs 76 of the constrictor ring 70 are spaced an equidistant predetermined distance apart from each other and have a predetermined width around the conical portion 74. The tabs 76 inhibit the conical portion 74 of the constrictor ring 70 from stretching during use. The areas between each of the tabs 76 form "expansion joints" in the conical portion 74 which tend to stretch more easily when vacuum is applied to the vacuum tube 20 and the base 7 of male genital 5 inflates. The tabs 76 are ribbed on their outside surface 82 to provide a more grippable surface.

A tubular shaped loader 100 having an open end 102 is provided to facilitate placement of the constrictor ring around the base 7 of the male genital 5. The constrictor ring 70 is inserted around a narrow end 104 of the loader 100. The individual can then grip the tabs 76 of the constrictor ring 70 and slide the constrictor ring down the length of the loader to the open end 102. The larger diameter of the open end 102 stretches the diameter of the conical and tubular portions 74 and 72 of the constrictor ring 70 to facilitate placement on the base 7 of the flaccid penis. The loader 100 may have grooves 106 formed in it to help reduce the force needed to slide the constrictor ring down the length of the loader.

OPERATION OF THE DEVICE

Although the operation of the present invention should be understood based on the above description, the following is provided to more easily explain the operation of the device 10. The device 10 can be provided in the form of a kit that can be purchased and taken to the privacy of an individual's home. The kit includes a vacuum tube 20, a hand or automatic pump 40 with a corresponding flexible hose 42, a plurality of diaphragm seals 50 each having an inner openings of varying diameter, and a plurality of constrictor rings 70 each having an outer end 73 of varying inside diameter that cooperates with one of the diaphragms. The individual can then select the cooperating diaphragm seal 50 and constricting ring 70 that comfortably and effectively fit their male genital.

Figure 3:
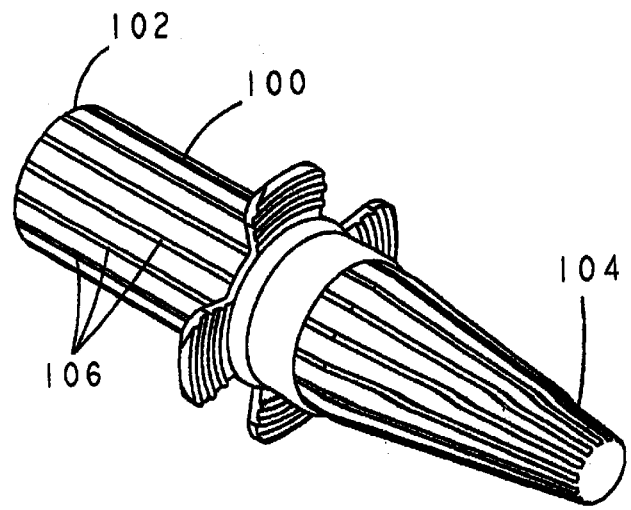
FIG. 3 is a perspective view of a constrictor ring of the present invention placed on a tube for installing the constrictor ring on the base of the male genital.

As shown in FIG. 3, the appropriate constrictor ring 70 is inserted onto the loader 100 and slid down to its open end 102. A dry powder, such as baby powder may be used to help decrease the force needed to slide the constrictor ring down the loader 100. The flaccid penis is then inserted into the open end 102 of the loader 100, and the constrictor ring 70 is slid off the loader and onto the penis 5 as close to its base 7 as possible. By using the tabs 76, the individual can work the constrictor ring 70 as far down the base 7 of the penis 5 as possible.

Figure 4:
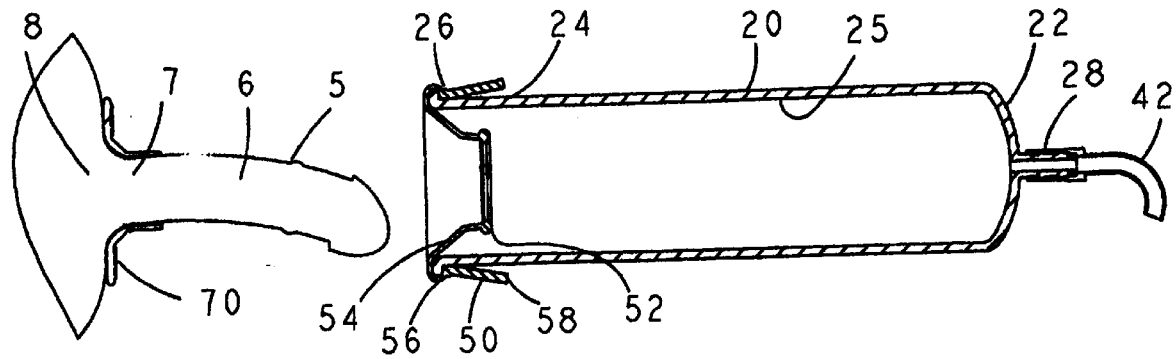
FIG. 4 is a cross-sectional view showing the constrictor ring secured to the base of a flaccid penis, and the vacuum tube and diaphragm seal aligned to receive the penis.
Figure 5:
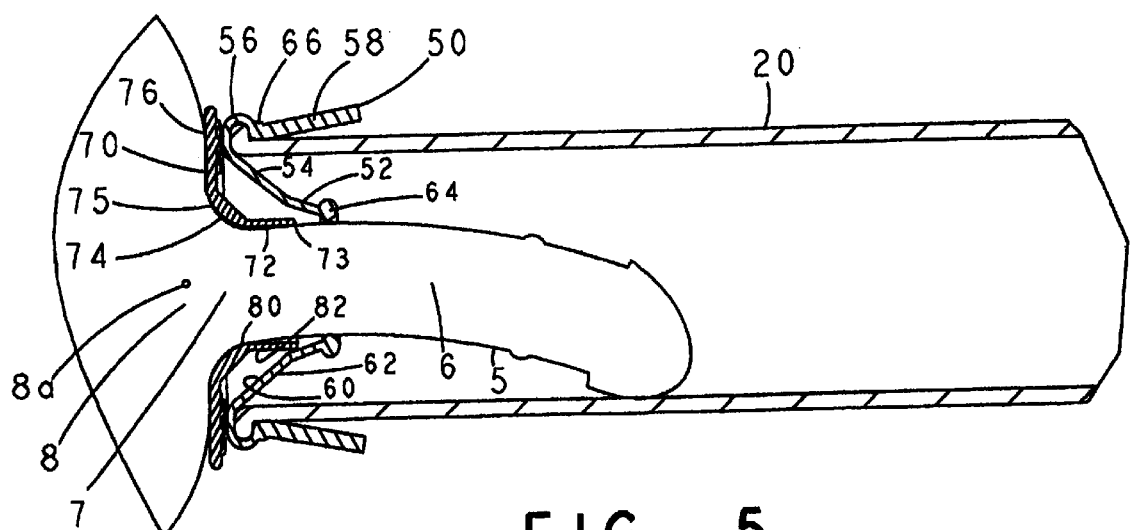
FIG. 5 is a cross-sectional view showing the penile erection device installed around the flaccid male genital with the diaphragm sealing directly around the male genital.

As shown in FIG. 4, the tip of the male genital 5 is then aligned with and placed against the opening in the inner end 52 of the diaphragm seal 50. The diaphragm seal is already secured to the open end 24 of the vacuum tube 20. The pump 40 is then activated to begin drawing air out of the tube 20. This causes the male genital 5 to be drawn into the tube 20 as shown in FIG. 5. Initially, the diaphragm 50 seals against the shaft 6 of the penis 5. This seal enables the pump to obtain an intermediate amount of vacuum pressure inside the vacuum tube 20. This intermediate amount of vacuum pressure causes the penis to begin inflating and begins to draw the root 8 of the penis 5 toward the constrictor ring 70. The vacuum pressure also causes the constrictor ring to move toward the inner end 52 of the diaphragm 50.

Figure 6:
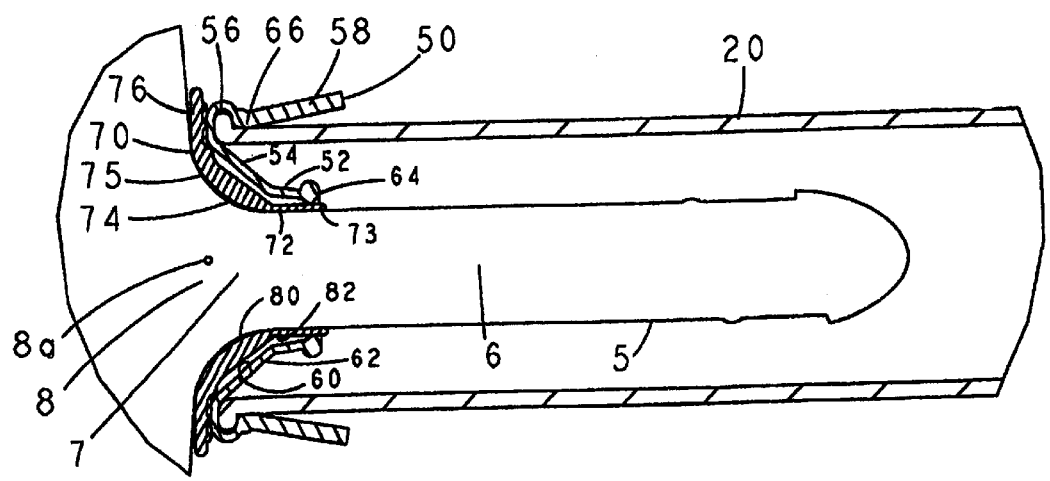
FIG. 6 is a cross-sectional view showing the penile erection device installed around a partially inflated male genital after a first predetermined amount of vacuum pressure has been produced inside the vacuum tube and the root of male genital beginning and the constrictor ring beginning to be drawn into the tube so that the diaphragm seals against the constrictor ring to form a substantially air tight seal.

When a first predetermined amount of vacuum pressure is achieved inside the vacuum tube 20, the inside surface 60 of the inner shank 64 of the diaphragm 50 engages the outer end 73 of the constrictor ring 70 and slides up onto and seals against the outer surface 82 of the tubular portion 72 of the constrictor ring, as shown in FIG. 6. This forms a substantially air tight seal and enables the pump 40 to produce a greater amount of vacuum pressure inside the vacuum tube 20. The greater vacuum pressure can be in the range of about 17 to 24 inches of mercury below atmospheric pressure. The greater vacuum pressure causes the penis to achieve a more inflated state and draws the root 8 of the penis 5 into the constrictor ring 70. The greater vacuum pressure is also believed to cause some of the root 8 of the penis 5 to inflate. The inflation of the base 7 and root 8 of the penis 5 cause the shaft 6 of the penis to raise up to produce a more natural and usable erection as shown in FIG. 7.

Figure 7:
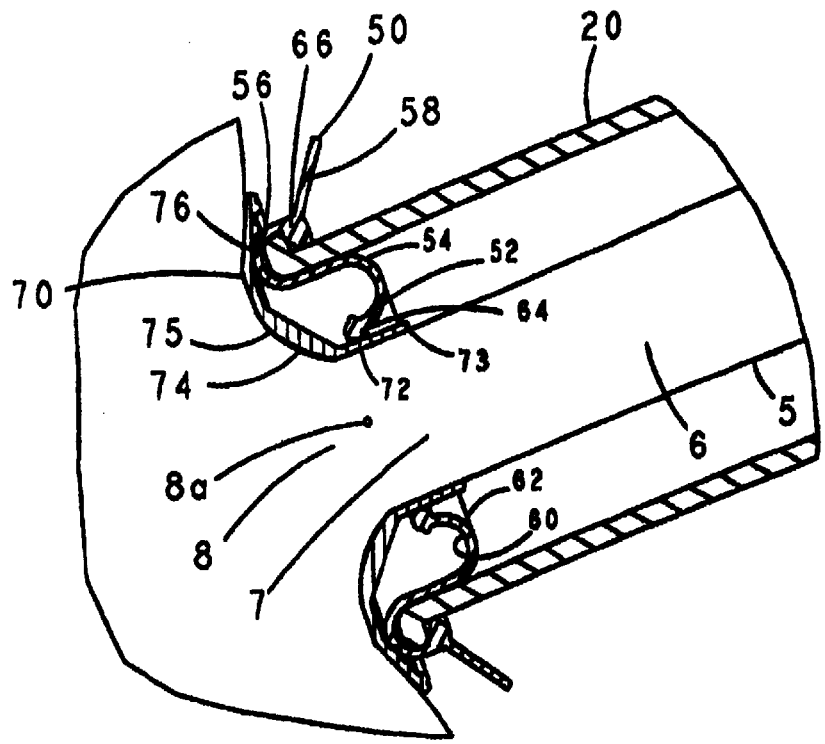
FIG. 7 is an enlarged cross-sectional view showing the diaphragm after a second predetermined amount of vacuum pressure has been produced inside the vacuum tube and the inner end of the diaphragm has inverted so that the diaphragm forms an "S" shape and a portion of the root of the male genital has passed into the constrictor ring.

After the diaphragm 50 seals against the constrictor ring 70 and a second predetermined amount of vacuum pressure is achieved inside the vacuum tube 20, the inner end 52 of the diaphragm 50 may invert so that the diaphragm forms an "S" shape as shown in FIG. 7. After the inversion into the "S" shape has occurred, the outside surface 62 of the inner shank 64 of the diaphragm 50 is in contact with and seals against the outside surface 82 of the constrictor ring 70. The amount of vacuum pressure needed to achieve the first and second predetermined amounts of pressure will vary from individual to individual depending on a variety of factors such as the size, shape and characteristics of the male genital 5, diaphragm 50 and constrictor ring 70.

Figure 8:
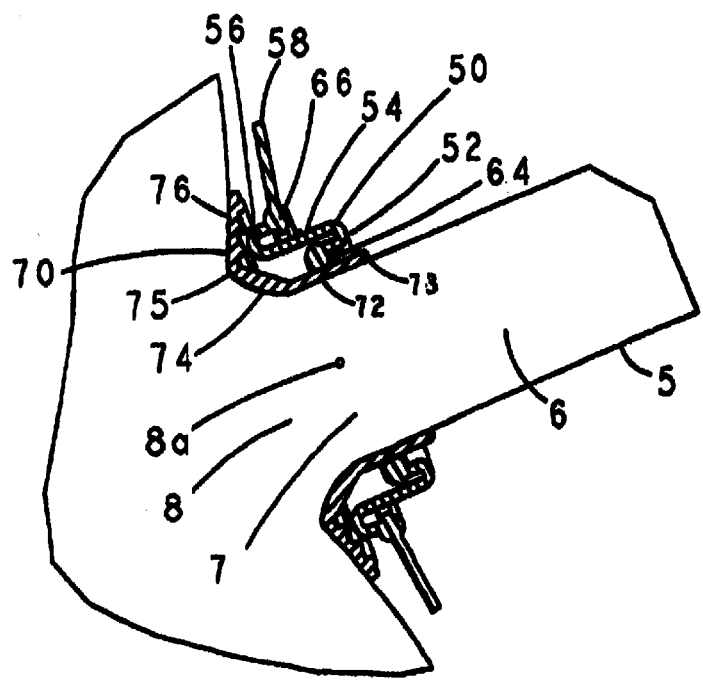
FIG. 8 is an enlarged cross-sectional view showing the constrictor ring secured to the base of the penis and the diaphragm released from the vacuum tube.
Figure 9:
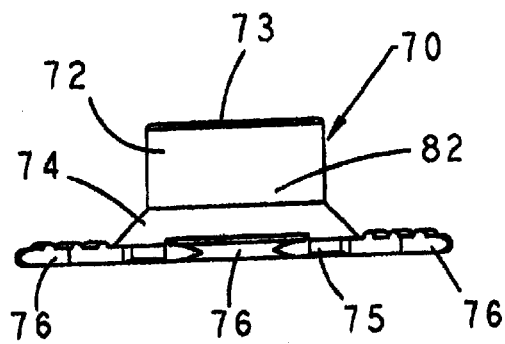
FIG. 9 is a side view of the constrictor ring with a four tab design.

The pump 40 is then turned off and the flexible hose 42 is disconnected from the nippled opening 28 of the vacuum tube 20 to release the vacuum pressure from inside the tube 20. The individual then disconnects the diaphragm seal 50 from the vacuum tube 20 by use of the handles 58, as shown in FIG. 8. The diaphragm 50 collapses against and remains on the constrictor ring 70. The penis 5 remains in its natural erect position after the vacuum tube 20 is removed because it is believed that some of the root 8 has been drawn into the constrictor ring 70 so that the blood is retained in the inflated root.

It will be understood that the invention may be embodied in other specific forms without departing from the spirit or central characteristics of the invention. The present examples and embodiments of the invention are to be considered in all respects as illustrative and not restrictive, and the invention is not to be limited to the details given herein.

Having described our invention, what we claim as new and desire to secure by Letters Patent of the United States is:

1. A penile erection device for causing the erection of a male genital, said penile erection device comprising:
    a vacuum tube having an open end and an inside adapted to receive the male genital;
    a flexible diaphragm seal having inner and outer ends, said outer end sealing around said open end of said vacuum tube; and,
    a constrictor ring adapted to be placed on the male genital, said inner end of said diaphragm sealing around said constrictor ring.

2. The penile erection device of claim 1, wherein said diaphragm is adapted to engage and seal around the male genital prior to applying vacuum pressure to said inside of said vacuum tube, and wherein said constrictor ring seals against said diaphragm when vacuum pressure is applied to said inside of said vacuum tube.

3. The penile erection device of claim 2, wherein said diaphragm has inside and outside surfaces, and when a first predetermined amount of vacuum pressure is achieved inside said vacuum tube, said inside surface of said diaphragm seals against said constrictor ring, and when a second predetermined amount of vacuum pressure is achieved inside said vacuum tube, said diaphragm inverts to form an "S" shape and said outside surface of said diaphragm seals against said constrictor ring.

4. The penile erection device of claim 1, and wherein said constrictor ring has an inside surface and inner and outer ends, and said outer end has an inside surface of a predetermined diameter, and said predetermined diameter of said inside surface continuously increases heading from said outer end toward said inner end.

5. The penile erection device of claim 1, and wherein said constrictor ring has inner and outer ends, a conical portion located proximal said inner end of said constrictor ring and a tubular portion located proximal said outer end of said constrictor ring, and said conical and tubular portions are joined together.

6. The penile erection device of claim 5, and wherein said inner and outer ends of said inner surface of said constrictor ring are rounded for comfort, and wherein said constrictor ring has an outer surface, and said outer end of said outer surface of said constrictor ring is rounded to facilitate sliding engagement of said diaphragm around said constrictor ring when vacuum pressure is applied to said inside of said vacuum tube.

7. The penile erection device of claim 5, and wherein said constrictor ring includes a plurality of tabs extending from said inner end of said constrictor ring.

8. The penile erection device of claim 7, and wherein said tabs extend from said conical portion of said constrictor ring at spaced locations around said conical portion to form expansion joints in said conical portion between said tabs.

9. The penile erection device of claim 1, wherein said diaphragm seal has handles integrally molded to said outer end of said diaphragm.

10. The penile erection device of claim 1, and further comprising means for removing air from said vacuum tube.

11. The penile erection device of claim 1, wherein said penile erection device achieves vacuum pressures of at least about 17 inches of mercury in vacuum pressure.

12. A penile erection kit for providing a custom fit to a male genital of an individual, said kit comprising:

a vacuum tube having an open end of predetermined diameter and an inside;

a plurality of constrictor rings, each of said constrictor rings having a different predetermined diameter, said constrictor rings adapted to be placed around the male genital; and, a plurality of diaphragms, each of said diaphragms having inner and outer ends, said outer end of each of said diaphragms having a predetermined diameter adapted to engage and seal around said open end of said tube, and said inner end of each of said diaphragms having a different predetermined diameter that corresponds to said predetermined diameter of one of said constrictor rings, said corresponding diaphragm engaging and sealing around said selected constrictor ring.

13. The penile erection kit of claim 12, and further comprising means for removing air from said vacuum tube.

14. The penile erection kit of claim 12, and further comprising a tube shaped loader for facilitating placement of said constrictor ring on the male genital.

\* \* \* \* \*